United States Patent [19]

Miller

[11] Patent Number: 4,934,936
[45] Date of Patent: Jun. 19, 1990

[54] DENTAL ANCHOR FOR RETENTION OF DENTAL RESTORATION

[75] Inventor: Alan N. Miller, New City, N.Y.

[73] Assignee: IPCO Corporation, White Plains, N.Y.

[21] Appl. No.: 239,432

[22] Filed: Sep. 1, 1988

[51] Int. Cl.⁵ ............................................... A61C 5/08
[52] U.S. Cl. ..................................... 433/220; 433/221; 433/225
[58] Field of Search ........................ 433/220, 221, 225

[56] References Cited

U.S. PATENT DOCUMENTS

| | | | |
|---|---|---|---|
| 328,837 | 10/1885 | Case | 433/231 |
| 907,949 | 12/1908 | Billow | 433/220 |
| 4,600,392 | 7/1986 | Weissman | 433/225 |

FOREIGN PATENT DOCUMENTS 2360552  6/1975  Fed. Rep. of Germany ...... 433/220

*Primary Examiner*—Robert Peshock
*Attorney, Agent, or Firm*—Helfgott & Karas

[57] ABSTRACT

A dental post for retention a dental restoration onto a prepared tooth stub, includes an elongated cylindrical portion insertable into the tooth stub and a head portion extending from the surface of the tooth stub for securement within the dental restoration. The head portion of the post is anatomically shaped to conform to the shape of the dental restoration.

28 Claims, 3 Drawing Sheets

DENTAL ANCHOR FOR RETENTION OF DENTAL RESTORATION

BACKGROUND OF THE INVENTION

This invention relates to a dental post which is normally securely inserted into a tooth stub for retention of a dental restoration on to the tooth stub.

Endodontic dental posts typically have a substantially cylindrical body portion insertable into the tooth stub and a head portion protruding outwardly from the tooth stub and holding a dental restoration thereon.

It has been known in the field of dentistry to build up a dental restoration onto a tooth stub for reconstruction of dentition. The tooth stub is preliminarily prepared by cutting it down to provide a suitable support on which the dental restoration will be placed. The apical section of the canal is sealed with gutta percha. A bore is drilled into the tooth, along the canal. Then a dental post is inserted into the bore formed in the tooth stub. The body portion of the dental post is normally provided with grooves or threads formed thereabout for enhancing the retention of the post by cement surrounding the post. The head portion of the dental post extends upwardly above the upper surface of the tooth stub so that as a dental restoration is built up onto the tooth stub it is retained in place on the tooth stub by the head portion of the dental post. After the dental post has been inserted into the bore of the tooth stub and cemented therein a core is built up on the head portion of the dental post. The final restoration is then built up around the core.

Head portions of the dental posts used in the field of dentistry until now are typically of a flattened tang shape. The problem with such otherwise satisfactory head portions of the dental posts is that sharp corners of the end of such a head portion and also in the region of a transition between the cylindrical body portion of the dental post and the head portion cause cracks in the core material and which cracks can occur around the sharp corners.

Additionally, because of the flattened tang, there will be more of the tang embedded in core material in the mesio-distal direction than in the labial-lingual direction. This causes uneven amounts of core material surrounding the post with a corresponding unevenness in the curing of the core material.

Accordingly, there is need for a dental post with a rounded head portion and which would ensure a more even spacing for the core material at all sides of the head portion.

SUMMARY OF THE INVENTION

It is therefore an object of the present invention to provide an improved dental post.

It is another object of the present invention to provide a dental post which would reduce the possibility of cracks caused by stress concentrations occurring on the core and the restoration to be built up on the head portion of the dental post.

Yet another object of the present invention is to provide a dental post which provides more uniform shrinkage in the core and the dental restoration.

Still another object of the present invention is to provide a more uniform head portion to provide a better uniformity in the thickness of a dental restoration built up on the head portion of the dental post.

Briefly, in accordance with the present invention, there is provided a dental post for retaining a dental restoration onto a prepared tooth stub which comprises an elongated body portion for insertion into a bore formed in the tooth stub, and a head portion joining the body portion at a neck portion and projecting from the tooth stub for securement within the restoration. The head portion is anatomically shaped to conform to the shape of the restoration.

In an embodiment, the head portion is terminated in a distal end which is wider than said neck portion both on the mesio-distal orientation and in the labial-lingual orientation.

In an embodiment of the invention, the head portion has an upper portion adjacent its upper end and being of substantially oval configuration and a lower portion adjacent the neck portion and being of substantially oval configuration. The oval configurations of the upper and lower portions are orthogonally oriented.

In an embodiment of the invention, the upper portion of substantially oval configuration has a major axis for orientation in the mesio-distal direction and the lower portion of substantially oval configuration has a major axis for orientation in the labial-lingual direction.

In another embodiment of the invention, the dental post further comprises a smooth and continuous transition between the upper portion and the lower portion.

In another embodiment, the head portion contours outwardly in a first orthogonal direction and contours inwardly in a second orthogonal direction in a region between the upper portion and the lower portion of the head portion. The outwardly contoured head portion is slightly skewed towards one side.

The body portion of the dental post is substantially cylindrical and may be provided on its periphery with various means which aid in securing the post in the bore of the tooth stub.

In one embodiment the securing means includes a thread formed along said body portion.

In another embodiment the securing means includes a plurality of externally spaced helical flutes disposed along said body portion.

In an embodiment of the invention, the body portion comprises at least one elongated leg projecting from the body portion for extending into the bore of the tooth stub.

In another embodiment of the invention, two elongated legs diametrically opposing each other are provided on said body portion. One of the legs may extend over a greater length of the body portion than the other leg.

In yet another embodiment of the invention the dental post for a posterior tooth comprises an elongated body portion for insertion into a bore formed in the tooth stub, and a head portion joining the body portion at a neck portion and projecting from the tooth stub for securement within the restoration. The head portion is of substantially oval configuration.

In another embodiment of the invention, the head portion includes a rounded head having a downwardly tapering end portion merging into a widening portion adjoining the neck portion of the post.

The aforementioned objects, features and advantages of the invention, will, in part, become obvious from the following more detailed description of the invention, taken in conjunction with the accompanying drawing, which forms an integral part thereof.

DETAILED DESCRIPTION OF THE PREFERRED EMBODIMENTS

Figure 1:
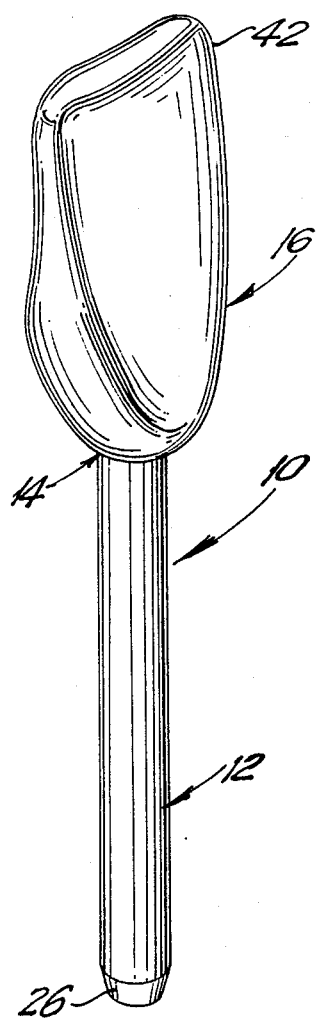
FIG. 1 is a perspective view of the dental post according to a first embodiment of the invention.
Figures 6A, 6B, 10:
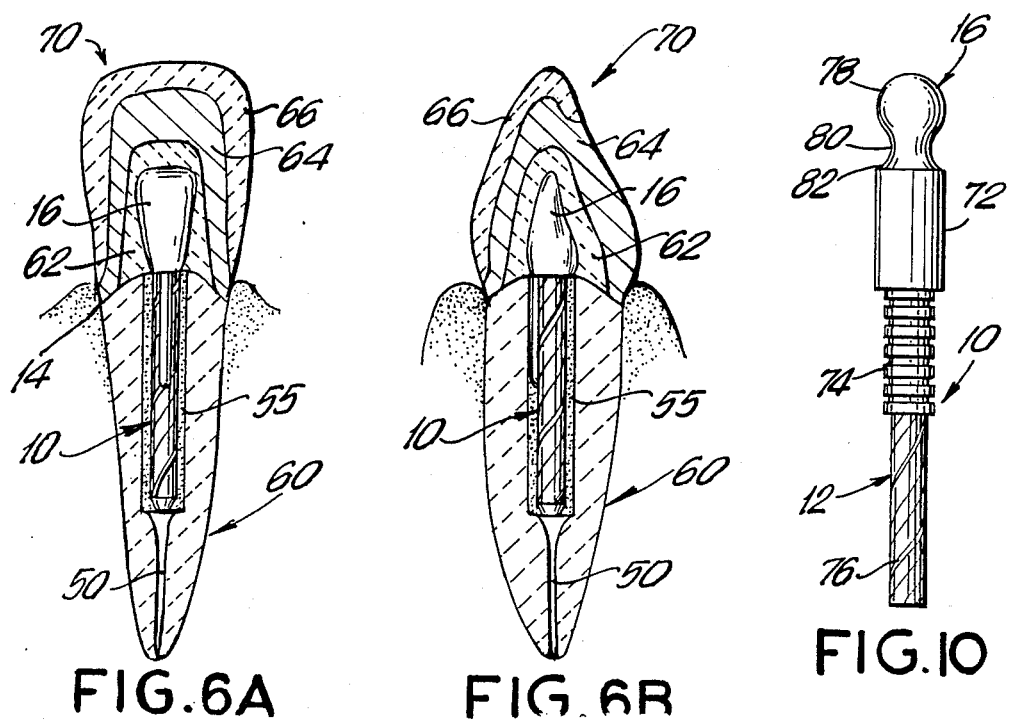
FIG. 6A is a sectional view through a tooth stub taken in the mesio-distal direction with a dental post and a dental restoration built up thereon.
FIG. 6B is a sectional view through the tooth stub similar to that of FIG. 6A but taken in the labial-lingual direction.
FIG. 10 is an elevational view of yet another embodiment of the invention.

Referring now to FIG. 1, the dental post of the present invention is shown generally at FIG. 10. The post includes an elongated cylindrical body portion 12, a neck portion 14 at the upper end of body portion 12 and a head portion 16.

Figure 2:
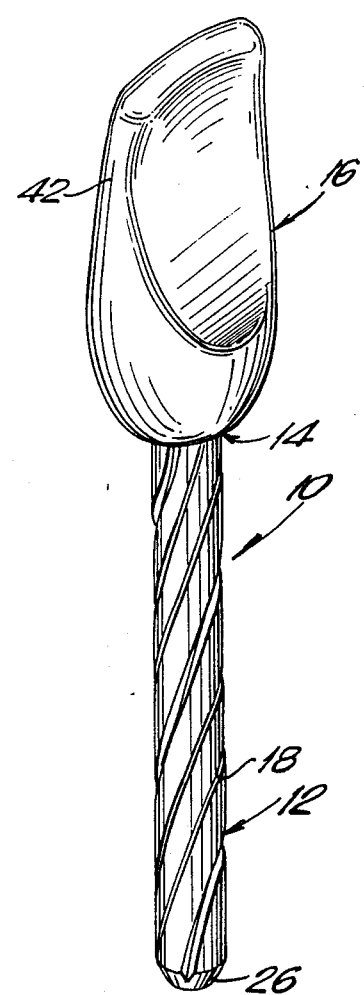
FIG. 2 is a perspective view of another embodiment of the dental post and showing a head portion similar to that of FIG. 1, but taken from the opposite side.

In the embodiment shown in FIG. 2 the cylindrical body portion 12 is provided with a plurality of helical flutes 18 formed about the periphery of the body portion 12. Flutes 18 are generally known in the dental posts of the foregoing type. Flutes 18 have a very large pitch. The pitch of each flute may be greater than the length of the body portion 12 so that a large number of separate helices can be provided. FIG. 2 shows the side of the head portion which is opposite to its side seen from FIG. 1.

Figure 3:
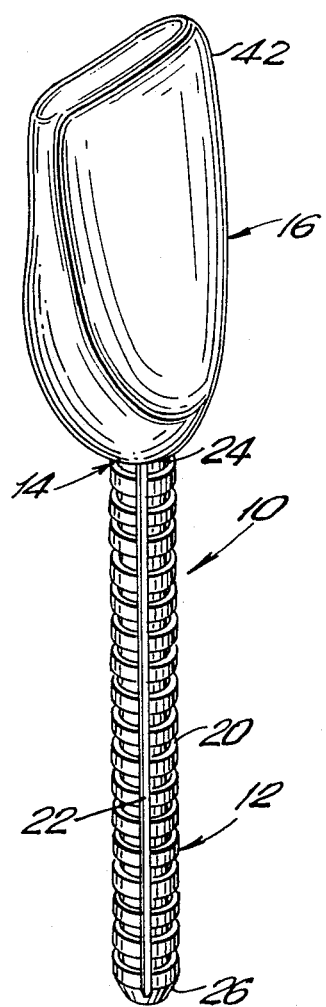
FIG. 3 is a perspective view of yet another embodiment of the invention.

In the embodiment of FIG. 3, the elongated body portion 12 has an external helical thread 20 formed about its outer surface. An elongated slot 22 is axially formed into the outer surface of the body portion 12 and cuts into the grooves of the thread. The slot starts at the upper end at the neck portion 14 and extends along substantially the entire length of the body portion 12. Two identical slots 22 can be provided at two diametrically opposing sides of the body portion 12.

In all three embodiments the lower end 26 of the body portion 12 is slightly tapered. Flutes 18 and threads 20 as well as slots 22 serve a double purpose. They prevent the post from moving within the bore in the tooth stub by receiving cement therein, and also provide a plurality of vents which are available for escape of the air from the bore as the pin 12 of the dental post is inserted into the bore of the tooth stub, to reduce hydrostatic pressure in the tooth stub.

Figures 4, 5:
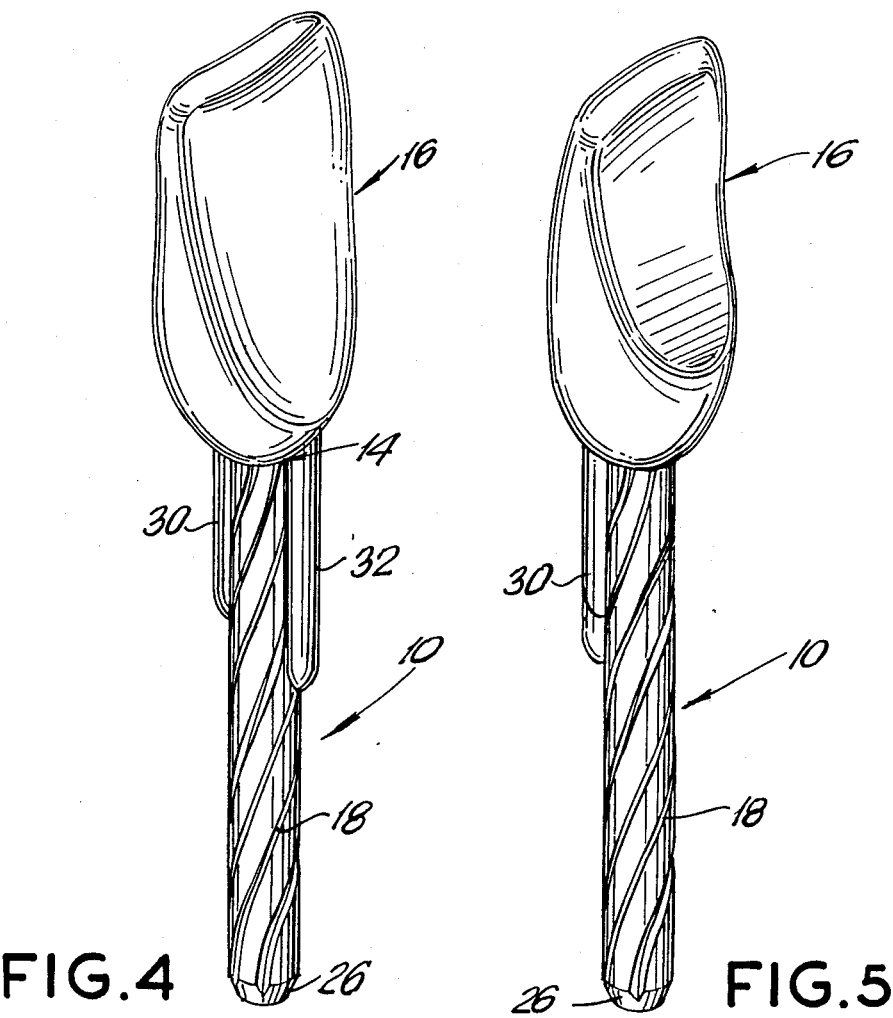
FIG. 4 is a perspective view of a further embodiment of the dental post.
FIG. 5 is a perspective view of another embodiment of the dental post.

FIGS. 4 and 5 illustrate further embodiments of the dental post according to the invention. The dental post 10 shown in FIG. 4 has large pitch flutes 18 similarly to those shown in FIG. 2 and, and in addition a pair of projecting legs or ribs 30 and 32 which are positioned in diametrical opposed relationship. Each of the ribs are elongated and commence from the neck portion 14. Each rib 30, 32 extends longitudinally downwardly along a portion of the length of the body portion. Leg 32 extends over a greater length of the pin 12 than leg 30. Legs 30 and 32 lie along the labial-lingual direction. The diametrically opposing ribs 30, 32 form in combination with the cylindrical body portion 12 an approximately oval shape which more suitably conforms to the actual shape of the canal in the tooth stub. Ribs or legs 30, 32 also have a retention function to further ensure securement of the dental post cemented in the bore of the tooth stub. FIG. 5 shows a single leg or rib 30 in contradistinction to two ribs 30, 32 of FIG. 4. The head portions 16 as well as lower tapered ends 26 of the dental posts of FIGS. 4 and 5 are identical to those of the aforedescribed embodiments of FIGS. 1 to 3. FIGS. 4 and 5 show two opposite sides of the head portion 16.

Figure 7:
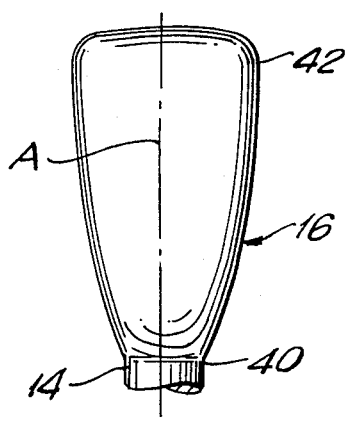
FIG. 7 is a front view of the head portion of the dental post.
Figure 8:
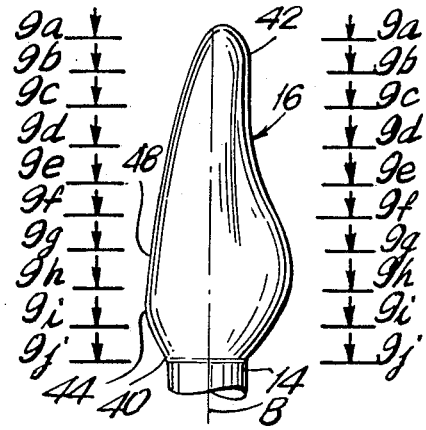
FIG. 8 is a side view of the head portion of a dental post.
Figure 9A:
FIG. 9a is a cross-sectional view taken along line 9a—9a of FIG. 8.
Figure 9F:
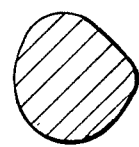
FIG. 9f is a cross-sectional view taken along line 9f—9f of FIG. 8.
Figure 9B:
FIG. 9b is a cross-sectional view taken along line 9b—9b of FIG. 8.
Figure 9G:
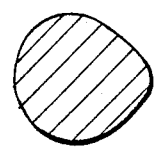
FIG. 9g is a cross-sectional view taken along line 9g—9g of FIG. 8.
Figure 9C:
FIG. 9c is a cross-sectional view taken on line 9c—9c of FIG. 8.
Figure 9H:
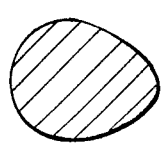
FIG. 9h is a cross-sectional view taken along line 9h—9h of FIG. 8.
Figure 9D:
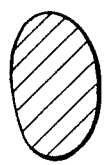
FIG. 9d is a cross-sectional view taken on line 9d—9d of FIG. 8.
Figure 9I:
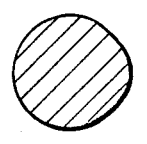
FIG. 9i is a cross-sectional view taken along line 9i—9i of FIG. 8.
Figure 9E:
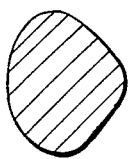
FIG. 9e is a cross-sectional view taken on line 9e—9e of FIG. 8.
Figure 9J:
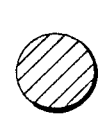
FIG. 9j is a cross-sectional view taken along line 9j—9j of FIG. 8.

The head portion 16 of the dental post 10 shown in the embodiments of FIGS. 1 to 5 will now be discussed in detail with reference to FIGS. 7, 8 and 9a to 9j. FIG. 7 shows a front view of the head portion 16 joined with the neck portion 14 while FIG. 8 shows a side view of the head portion of the dental post. In general the head portion 16, onto which can be built up in a known manner a dental core for supporting a dental restoration, has the shape which conforms to the anatomical shape of the missing tooth and therefore the shape of the dental restoration which is to be supported on the dental post. The head portion 16 shown in FIGS. 1 to 8 is particularly suitable for anterior teeth. As best seen in FIGS. 7 and 8 the head portion 16 terminates in a medial end 40 which is wider than the neck portion 14 both in the mesio-distal orientation and in the labiallingual orientation. Furthermore, as also seen in FIGS. 7 and 8, an undercut for grasping and retaining cement is provided at the transition zone between the medial end 40 and the neck portion 14. An oval shape of the head portion 16 results in two opposing directions. Due to a curved smooth undercut at the distal end 40 of the head portion no stress is exerted when the dental core is built up upon the head portion. Since the head portion 16 has no sharp corners the possibility of cracks in the core or the restoration is reduced and the surface of the tooth stub from which the head portion 16 projects will be better protected when the body portion 12 is secured in the bore of the tooth stub.

The oval configurations of the head portion are provided at its upper end and its medial or lower end as well in two orthogonal directions. A substantially oval upper portion 42 of the head portion 16 has a major axis designated at A on FIG. 7 for orientation in the mesio-distal direction while a substantially oval lower portion 44 has a major axis denoted at B in FIG. 8 for orientation in the labial-lingual direction. The upper portion 42 merges into the lower portion 44 at a smooth and continuous transition portion 48 (FIG. 8). This transition portion is bent outwardly in one orthogonal direction and is bent inwardly in a second orthogonal direction. The outwardly bent portion of the dental post head is slightly skewed towards one side as best seen in FIG. 8. The bent orientation of the head portion not only aids in retaining a dental core and a dental restoration on the dental post inserted into the tooth stub but also, in connection with anterior teeth, this orientation serves to properly position the dental restoration on the head portion since, as shown, anterior teeth are angularly shaped.

As clearly seen in FIGS. 9a to 9j a continual substantially oval cross-section in each of two orthogonal axes from the upper end of the head portion 16 to its lower end results. The head portion 16 is wider at the top than at the lower end in the mesio-distal direction. All the corners of the head portion 16 are rounded. The restoration material can be applied uniformly around the core formed on the head portion. Since the restoration material may be of light-curing material it cures better if it is of a uniform thickness. The smooth oval shape of the head portion 16 which conforms to the anatomical shape of the tooth ensures such a uniform thickness of core material around the head portion 16. Also, the smooth even configuration of the head portion of the dental post offers less shrinkage of the restoration material as compared to that occurring with conventional dental posts.

Referring now to FIGS. 6A and 6B which illustrate the dental post 10 inserted into the tooth stub bore in two mutually normal directions it will be seen that after an apical canal 50 is filled with gutta percha as is known, and the dental post 10 is placed into a bore 55 of the tooth stub 60 so that its head portion 16 projects outwardly from the tooth stub a composite or plastic material buildup in the form of a core 62 is formed on the extending head portion 16 of the dental post. The core 62 can be generally shaped by the dentist. Appropriate impressions are then made and sent to a laboratory for the formation of a metal crown casting 64. As best shown in FIG. 6A, tapering on the core allows impressions to be easily taken. A plastic or porcelain crown 66 formed on the metal casting 64 at the laboratory is fitted by the dentist on the core 62 in a conventional manner, to complete a dental restoration 70.

The dental restoration 70 is retained in place by the head portion 26 due to its anatomical shape and the undercuts at the neck portion 14 of the dental post, which undercuts grasp cement which securely holds the post, the core and the dental restoration together. FIGS. 6A and 6B show the dental restoration 70 as an anterior tooth.

FIG. 10 shows a dental post 10 for a posterior tooth. The dental post shown includes a stepped cylindrical body portion 12 which has three cylindrical sections of different diameters wherein an uppermost section 72 is of the greater diameter than an intermediate section 74 which in turn is of a greater diameter than that of a lower section 76. Either of the three cylindrical portions may be provided with helical flutes or be threaded, and can have slot-like vents to aid in retaining of the dental post in the tooth stub and form grooves for air escape from the tooth stub. Preferably, the uppermost section is left smooth without any retention means.

The head portion 16 of the dental post for a posterior tooth has also a substantially oval configuration and includes an upper portion of uniform shape which merges at a continual smooth tapering transition zone 80 into a widening lower portion 82. The head portion 16 is uniform at all sides. The top portion 72 may be solid.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A dental anchor for retaining a dental restoration onto a prepared tooth stub, comprising an elongated body portion for insertion into a bore formed in the tooth stub; a head portion joining the body portion at a neck portion and projecting from the tooth stub for securement within the restoration, said head portion being anatomically shaped to conform to the shape of the restoration; and a smooth continuous transition between said neck portion and said head portion.

2. A dental post as in claim 1, wherein said head portion terminates in a medial end adjacent to said neck portion, said medial end being wider than said neck portion both in the mesio-distal orientation and in the labial-lingual orientation.

3. A dental post as in claim 1, wherein said head portion has an upper portion adjacent its upper end and being of substantially oval configuration and a lower portion adjacent said neck portion and being of substantially oval configuration, the oval configurations of said upper and lower portions being orthogonally oriented.

4. A dental post as in claim 3, wherein said upper portion of substantially oval configuration has a major axis for orientation in the mesio-distal direction and said lower portion of substantially oval configuration has a major axis for orientation in the labial-lingual direction.

5. A dental post as in claim 3, wherein in a region between said upper portion and said lower portion, said head portion contours outwardly in a first orthogonal direction and contours inwardly in a second orthogonal direction.

6. A dental post as in claim 5, wherein the outwardly contoured head portion is slightly skewed toward one side.

7. A dental post as in claim 1, wherein said body portion is substantially cylindrical.

8. A dental post as in claim 7, further comprising means for securing said body portion with cement within the bore of the tooth stub, said securing means being provided on a periphery of said cylindrical body portion.

9. A dental post as in claim 8, wherein said securing means includes a thread formed along said body portion.

10. A dental post as in claim 8, wherein said securing means includes a plurality of externally spaced helical flutes disposed along said body portion.

11. A dental post as in claim 8, wherein said securing means commences from said neck portion and terminates at a tapered end of said body portion.

12. A dental post as in claim 8, and comprising at least one elongated leg radially projecting from said body portion for extending into the bore of the tooth stub.

13. A dental post as in claim 12, wherein said leg extends longitudinally over a portion of the length of said body portion.

14. A dental post as in claim 13, wherein two elongated legs diametrically opposing each other are provided on said body portion.

15. A dental post as in claim 14, wherein one of said elongated legs extends longitudinally over a greater length of said body portion than another of said elongated legs.

16. A dental post as shown in claim 12, wherein said at least one elongated leg commences from said neck portion.

17. A dental post as in claim 14, wherein said two elongated legs extend in a plane lying along the labial-lingual direction.

18. A dental post as in claim 1, wherein said head portion comprises smooth rounded edges.

19. A dental anchor for retaining a dental restoration onto a prepared tooth stub, comprising an elongated cylindrical body portion having means for securing the body portion with cement when the body portion is inserted into the tooth stub; and a barrel-shaped head portion hined to said body portion said head portion including an upper portion of a substantially oval cross-section, a lower portion of a substantially oval cross-section, and a transition region continuously formed between said upper portion and said lower portion also of a substantially oval cross-section, said transition region forming between said upper and lower portion a peripheral undercut for packing a restoration material therein.

20. A dental anchor as in claim 19, wherein said oval cross-sections of said upper and lower portions are orthogonally oriented.

21. A dental anchor for retaining a dental restoration onto a prepared tooth stub, comprising an elongated body portion for insertion into a bore formed in the tooth stub; and a head portion joining said body portion at a neck portion and projecting from the tooth stub for securement within the restoration, said head portion being of substantially oval configuration, said neck portion continuously merging into said head portion and forming therewith a peripheral cavity which receives a restoration material and retains the same when the dental restoration is placed onto the prepared tooth stub.

22. A dental anchor as in claim 21, wherein said head portion includes a rounded head having a downwardly tapering end portion merging into a widening portion adjoining said neck portion.

23. A dental anchor as in claim 21, wherein said body portion is cylindrically stepped.

24. A dental anchor as in claim 23, wherein means for securing said body portion with cement within the bore of the tooth stub are provided on a periphery of said body portion.

25. A dental anchor as in claim 24, wherein said securing means include helical flutes formed along one step portion of said stepped pin and threads formed along another step portion of said stepped pin.

26. A dental anchor as in claim 25, wherein said body portion includes a solid step portion adjoining said neck portion.

27. A dental anchor for retaining a dental restoration onto a prepared tooth stub, comprising an elongated body portion; and a head portion joining said body portion at a neck portion and projecting from the tooth stub for securement within the dental restoration, said head portion having a smooth outer surface without any sharp edges to prevent a formation of cracks on a core or a restoration to be built upon said head portion, wherein said head portion includes at least one barrel-shaped portion between said neck portion and the top end of the head portion.

28. A dental anchor as in claim 27, wherein said head portion has at least one portion with a cross-section which widens from said neck portion towards a top end of the head portion in a mesiodistal direction.

* * * * *